(12) United States Patent
Mishima et al.

(10) Patent No.: US 7,276,054 B2
(45) Date of Patent: Oct. 2, 2007

(54) DISPOSABLE WEARING ARTICLE

(75) Inventors: Yoshitaka Mishima, Kagawa-ken (JP);
Kaiyo Nakajima, Kagawa-ken (JP);
Tomoko Sugito, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 237 days.

(21) Appl. No.: 10/686,812

(22) Filed: Oct. 17, 2003

(65) Prior Publication Data
US 2004/0138637 A1    Jul. 15, 2004

(30) Foreign Application Priority Data
Oct. 18, 2002    (JP) ............... 2002-304581

(51) Int. Cl.
*A61F 13/15*    (2006.01)
(52) U.S. Cl. ............ 604/385.01; 604/378; 604/385.19; 604/385.101; 604/385.12; 604/385.09
(58) Field of Classification Search ........... 604/385.01, 604/378, 380, 382, 383, 385.101, 385.19, 604/385.12, 385.09
See application file for complete search history.

(56) References Cited

FOREIGN PATENT DOCUMENTS

| EP | 1243237 A2 * | 9/2002 |
| JP | 2523711 | 10/1996 |
| WO | WO 98/22062 | 5/1998 |
| WO | WO 02/47594 A1 | 6/2002 |

* cited by examiner

*Primary Examiner*—Jacqueline F. Stephens
(74) *Attorney, Agent, or Firm*—Lowe, Hauptman, Ham & Berner, LLP (57) ABSTRACT

A disposable diaper as a disposable wearing article has a front waist region, a rear waist region and a crotch region extending between these two waist regions. The crotch region is formed on its surface facing a wearer's body with a protrusion formed by flexible and elastic foamed plastic prepared separately of an absorbent pad.

14 Claims, 11 Drawing Sheets

FIG. 11

DISPOSABLE WEARING ARTICLE

BACKGROUND OF THE INVENTION

The present invention relates to a disposable wearing article such as a disposable diaper.

JP Utility Model Registration Publication No. 2523711B discloses the disposable diaper provided in a crotch region of a liquid-absorbent core with a feces receiving concavity defined by a depressed upper surface of the core. A protrusion formed around this concavity is more flexible than the remaining portion of the core.

The well-known disposable diaper disclosed in the above-cited Publication allows the protrusion to be placed against a wearer's body more tightly around an anus than the remaining portion and thereby to receive discharged feces in the concavity without any anxiety of leakage. The protrusion is flexible sufficiently to eliminate the inconvenience that a wearer might experience uncomfortable feeling due to the protrusion tightly placed against the wearer's body, However, the core usually comprises fluff pulp or a mixture of fluff pulp and super-absorbent polymer particles and, once having been deformed under a body weight, it is difficult for the core to restore its initial shape. This problem becomes more serious after the core has been wetted with body fluids. With the well-known diaper disclosed in the above-cited Publication provided with the core having such undesired characteristics, the protrusion can not be held reliably in tight contact with the wearer's body for a long period. Furthermore, if the diaper is put again on the wearer' body after the same diaper has been put off from the wearer, there is a possibility that the protrusion could not come in tight contact with the wearer's body since the protrusion has been more or less flattened.

SUMMARY OF THE INVENTION

It is an object of the present invention to improve the disposable diaper adapted to receive bodily discharges in the concavity surrounded by the protrusion so that the protrusion can be held more reliably in tight contact with the wearer's body even for a long period or even again after once the same diaper has been put off from the wearer's body.

According to the present invention, there is provided a disposable wearing article having a front waist region, a rear waist region and a crotch region extending between these two waist regions, each having an inner surface facing a wearer's body and an outer surface facing away from the wearer's body, and the crotch region being formed on the inner surface with a protrusion lying in a transversely middle zone of the crotch region and at least partially surrounding at least one of an anus and a urethral of a wearer.

The protrusion comprises a flexible and elastic foamed plastic material.

The present invention can be exploited also in preferred embodiments as follow:

The protrusion comprises a block of the foamed plastic material.

The protrusion has a top facing the wearer's body and a bottom facing away from the wearer's body and comprises a cover sheet defining an outer surface of the protrusion and a filler with which an inner space defined by the cover sheet is filled, the filler comprises a plurality of chips of the flexible and elastic foamed plastic material.

The foamed plastic material is polyurethane foam having a cell population in a range of 30 to 150/25 mm, a density in a range of 20 to 120 kg/m$^3$ and an impact resilience in a range of 5 to 30%.

The block of the foamed plastic material is bonded to an upper surface of a liquid-pervious sheet covering an absorbent body.

The protrusion is formed in the crotch region and presents a substantially annular planar shape contoured by a front end segment located aside toward the front waist region, a rear end segment located aside toward the rear waist region and transversely opposite lateral segments extending between the front and rear end segments and wherein a height of the protrusion gradually increases toward at least one of the front and rear end segments and maximizes at an apex on a longitudinal center line of the wearing article.

The protrusion is formed in the crotch region and presents a U-shape contoured by a pair of lateral segments extending substantially parallel to a longitudinal center line of the wearing article and a curved end segment located aside to one of the front and rear waist regions and connecting the lateral segments to each other.

The protrusion is formed in the crotch region so as to be located aside toward the rear waist region A pair of the protrusions are formed in the crotch region so as to be located aside toward the front waist region and the rear waist region, respectively, and the protrusions are aligned with each other in a longitudinal direction of the crotch region.

The protrusion extends over the crotch region further into both the front waist region and the rear waist region.

A portion of the crotch region surrounded by the protrusion forms a pocket bulging out from an inner side toward an outer side of the diaper.

The apex of the protrusion describes a circular arc being convex upward as viewed in a cross-section of the protrusion.

The chips make up 100 to 60 wt % of the filler.

Each of the chips has a maximum diameter in a range of 1 to 20 mm.

Thermoplastic synthetic fibers make up 0 to 40 wt % of the filler.

The maximum diameter of the chips progressively increases from the apex toward the bottom of the protrusion.

A density of the chips progressively increases from the apex toward the bottom of the protrusion.

A layer of the thermoplastic synthetic fiber underlies the chips in a vicinity of the bottom and the layer of thermoplastic synthetic fiber has a bending stiffness in a range of 0.98 to 5.0 N/25.4 mm.

DETAILED DESCRIPTION OF THE PREFERRED EMBODIMENTS

Details of the disposable wearing article according to the present invention will be more fully understood from the description of a disposable diaper as a typical embodiment of the invention given hereunder with reference to the accompanying drawings.

Figure 1:
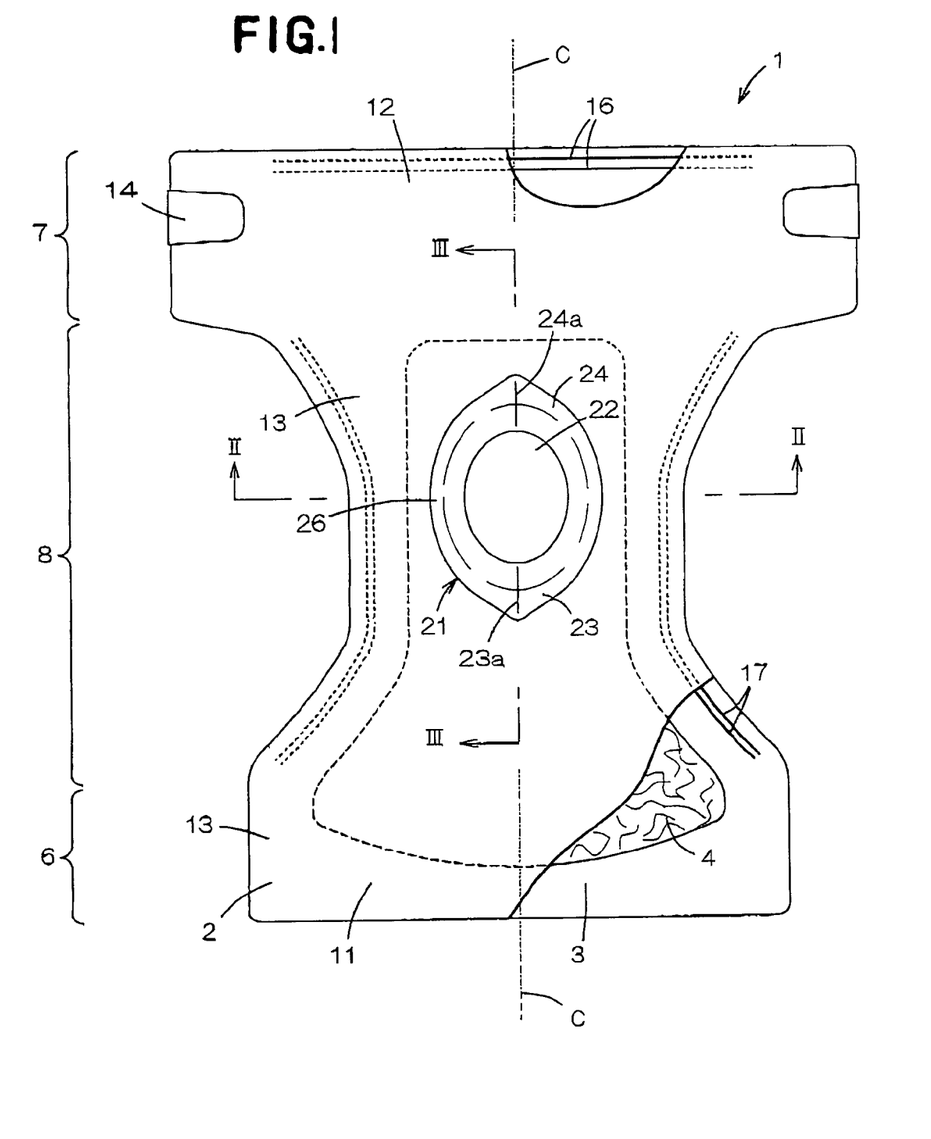
FIG. 1 is a partially cutaway plan view showing a diaper according to the invention.

A disposable diaper 1 illustrated in FIG. 1 in a partially cutaway perspective view comprises a liquid-pervious topsheet 2 defining an inner surface of the diaper 1 facing a wearer's body, a liquid-impervious backsheet 3 defining an outer surface of the diaper 1 facing wearer's clothes and a body fluid absorbent pad 4 interposed between a lower surface of the topsheet 2 and an upper surface of the backsheet 3. The top- and backsheets 2, 3 extend outward beyond a peripheral edge of the absorbent pad 4 and these extensions of the top- and backsheets 2, 3 are overlaid and joined together to form a front flap 11, a rear flap 12 and lateral flaps 13. In the rear flap 12 and the lateral flaps 13, waist elastic members 16 and leg elastic members 17 extend in waist's circumferential direction and in leg's circumferential direction, respectively. These elastic members 16, 17 are bonded in a stretched state to the lower surface of the topsheet 2 and/or the upper surface of the backsheet 3. In a vertical direction as viewed in FIG. 1, the diaper 1 defines a front waist region 6, a rear waist region 7 and a crotch region 8 extending between these two waist regions 6, 7 wherein the lateral flaps 13 in the rear waist region 7 are provided with a pair of tape fasteners 14, respectively. The diaper 1 is further provided in the crotch region 8 with a feces receiving space 22 surrounded by a protrusion 21 having an annular planar shape. More specifically, the protrusion 21 occupies a zone of the crotch region 8 put aside toward the rear waist region 7 or bestrides the boundary between the crotch region 8 and the rear waist region 7 so that the protrusion 21 may properly surround a wearer's anus.

Figure 2:
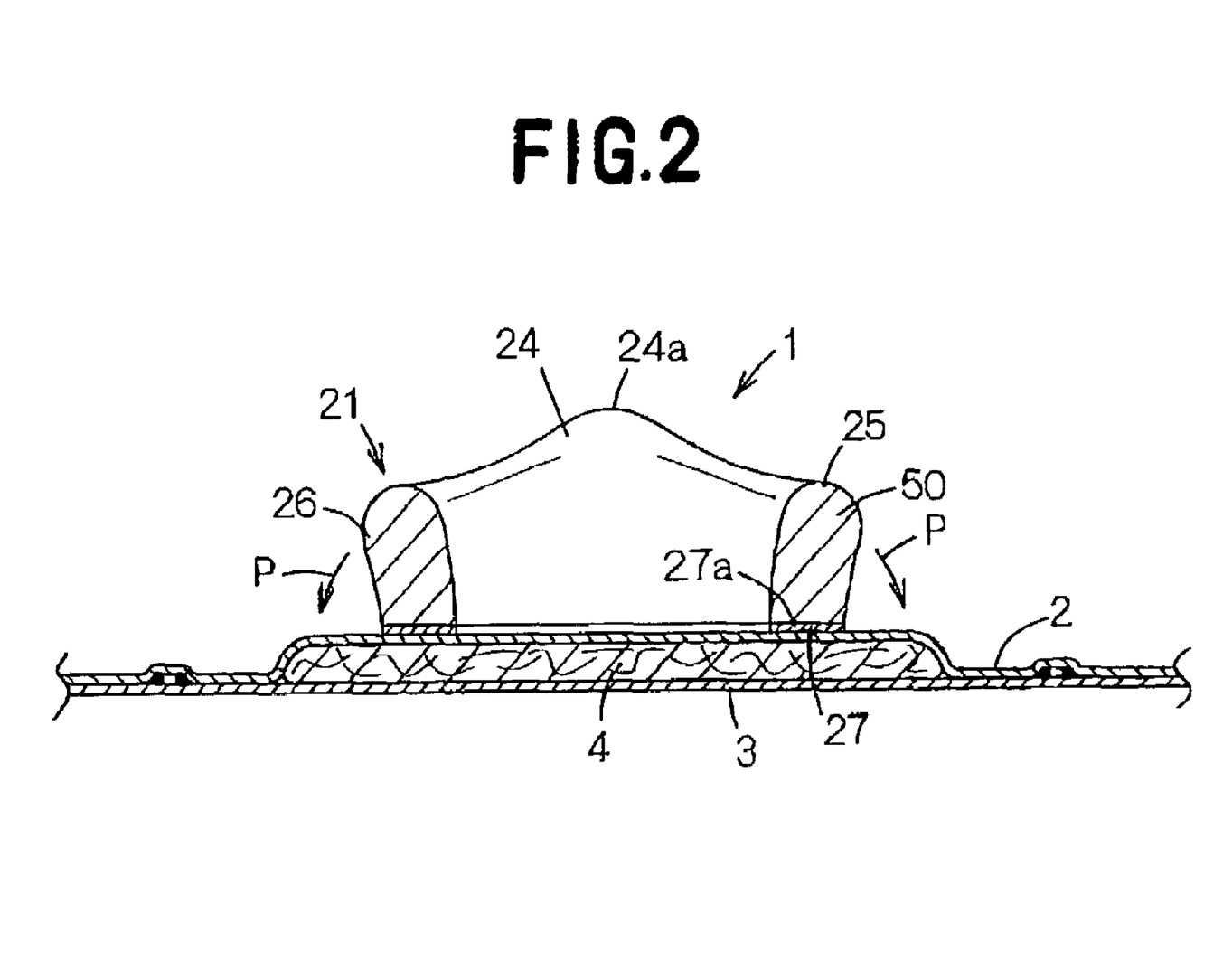
FIG. 2 is a sectional view taken along a line II-II in FIG. 1.
Figure 3:
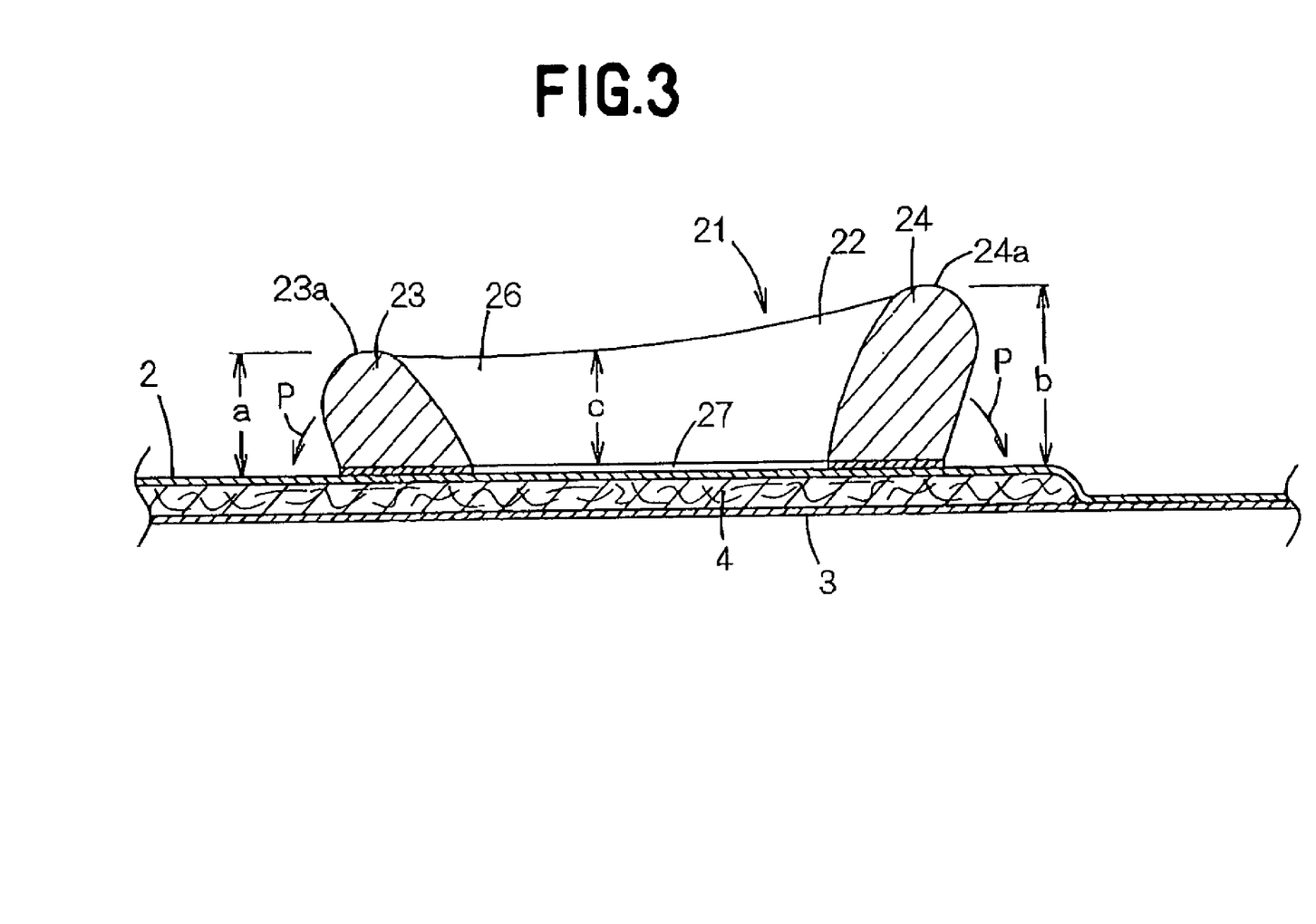
FIG. 3 is a sectional view taken along a line III-III in FIG. 1.

FIGS. 2 and 3 are sectional views taken along lines II-II and III-III in FIG. 1, respectively, and the line III-III coincides with a center line C-C bisecting a width of the diaper 1. The protrusion 21 has its planar shape being symmetric about the center line C-C. The protrusion 21 is contoured by a front end segment 23 placed aside toward the front waist region 6, a rear end segment 24 placed aside toward the rear waist region 7 and transversely opposite lateral segments 26 extending between the front and rear end segments 23, 24. Referring to FIGS. 2 and 3, the protrusion 21 has a top 25 facing the wearer's body and a bottom 27 facing away from the wearer's body wherein the bottom 27 is fixed to the topsheet 2 by means of an adhesive 27a. The front end segment 23, the rear end segment 24 and the lateral segments 26 of the protrusion 21 respectively have heights a, b, c as measured from the bottom 27 to the top 25. Preferably, the heights a, b, respectively have the maximum values on the center line C-C as illustrated and more preferably the upper ends of these front and rear end segments 23, 24 are pointed on the center line C-C. While the maximum value of the height a is preferably equal to or smaller than the maximum value of the height b, it is possible without departing from the scope of the invention to set the maximum value of the height a being larger than the maximum value of the height b. The height c of the lateral segments 26 may have a value equal to the height a or b, or an intermediate value between these two values a and b. The lateral segments 26 preferably tilt outward in the vicinity of the respective tops 25 so that a width between these lateral segments 26 may be gradually enlarged from the front and rear end segments 23, 24 toward the intermediate points (See FIG. 2). The respective tops 25 of these segments 23, 24, 26 appearing in the sectional view of the protrusion taken in the vertical direction describe circular arcs which are convex upward. The feces receiving space 22 is defined by the protrusion 21 and a portion of the topsheet 2 surrounded by the protrusion 21.

The diaper 1 configured in the manner as has been described above is put on the wearer's body with the protrusion 21 placed against the wearer's body so that the feces receiving space 22 may immediately underlie the anus. The protrusion 21 comprises a block 50 molded from foamed plastic having appropriate flexibility and elasticity to come in close contact with the wearer's body when the diaper is put on the wearer's body. In the preferred protrusion 21, the front end segment 23 as well as the rear end segment 24 are pointed upward in the vicinity of respective middle zones 23a, 24a (See FIG. 1) thereof and these upward pointed zones 23a, 24a are effective to solve one of the problem encountered by the diaper of prior art such that body fluids may often leak along the rump-cleft of the wearer. Such protrusion 21 is sufficiently flexible to avoid an anxiety that the protrusion 21 tightly placed against the wearer's body might stimulate the wearer's body. The block 50 of the foamed plastic forming this protrusion 21 preferably has the number of cells in a range of 30 to 150/25 mm as measured in accordance with the prescription 5.2 of JIS K 6400, an impact resilience in a range of 5 to 30% as measured by B method in accordance with prescription 9.2 of JIS K 6400, and a density in a range of 20 to 120 kg/m$^3$. The protrusion 21 preferably the respective heights a, b, c in a range of 5 to 50 mm. The planar shape of the protrusion 21 is not limited to the elliptical shape as illustrated but may be of the other shapes such as circular, oval and polygonal shapes. For example, the lateral segments 26 may be tilted outward to obtain the trumpet-shaped protrusion 21 defining the feces receiving space 22 of which the inner and outer diameters are gradually increased from the upper surface of the topsheet upward. The protrusion 21 shaped in this manner is deformed in a direction indicated by an arrow P under a body weight of the wearer exerted thereupon, that is, the inner diameter of the feces receiving space 22 is gradually enlarged and thereby the protrusion 21 facilitates the space 22 to receive discharged feces.

Figure 4:
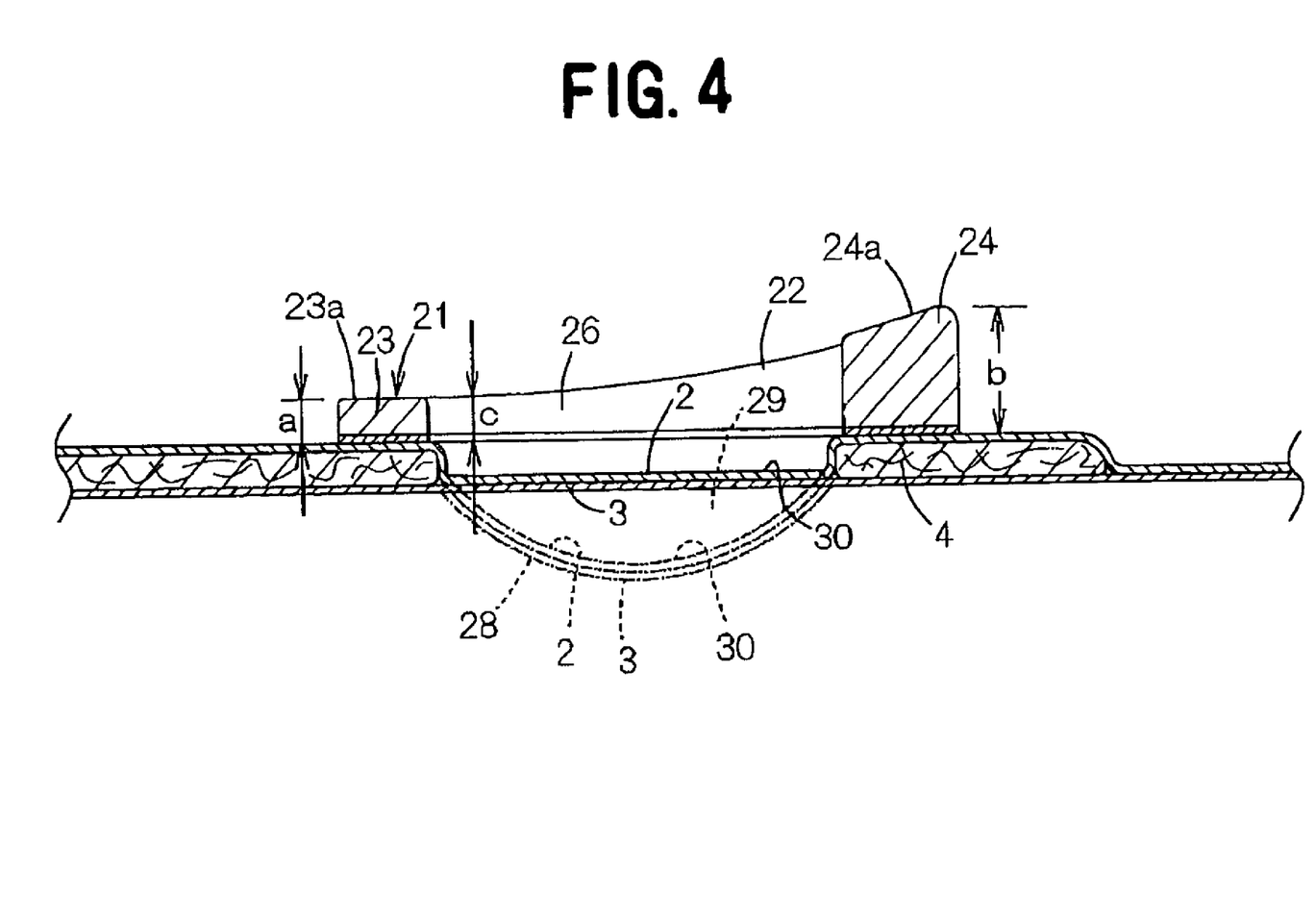
FIG. 4 is a view similar to FIG. 3 showing one embodiment of the invention.

FIG. 4 is a view similar to FIG. 3 showing one embodiment of the invention. In the diaper 1 according to this embodiment, a bottom 30 of the feces receiving space 22 includes no absorbent pad 4 and is defined by the topsheet 2 and the backsheet 3. This feces receiving space 22 is deeper than the previously described feces receiving space 22 in reference with FIG. 3 and has a correspondingly higher capacity. Moisture content of feces is absorbed by the absorbent pad 4 partially forming an inner peripheral wall of the feces receiving space 22. Imaginary lines 28 in FIG. 4 indicate an embodiment of the bottom 30 according to which the bottom 30 forms a pocket 29 bulging outward from the diaper 1 and thereby enlarges an inner volume of the feces receiving space 22. In the case of this diaper 1, the front end segment 23 of the protrusion 21 has its height a substantially equal to the height c of the lateral segments 26 at respective zones thereof located aside toward the front end segment 23. In this embodiment, the front end segment 23 is substantially flat, i.e., describes no circular arc in the vicinity of its top so as to define the pointed intermediate zone 23a. On the other hand, the rear end segment 24 has its intermediate zone 24a pointed upward. For the bottom 30, the topsheet 2 is not the essential element and the bottom 30 may be formed by the backsheet 3 alone or any other liquid-impervious sheet prepared separately of the backsheet 3.

Figure 5:
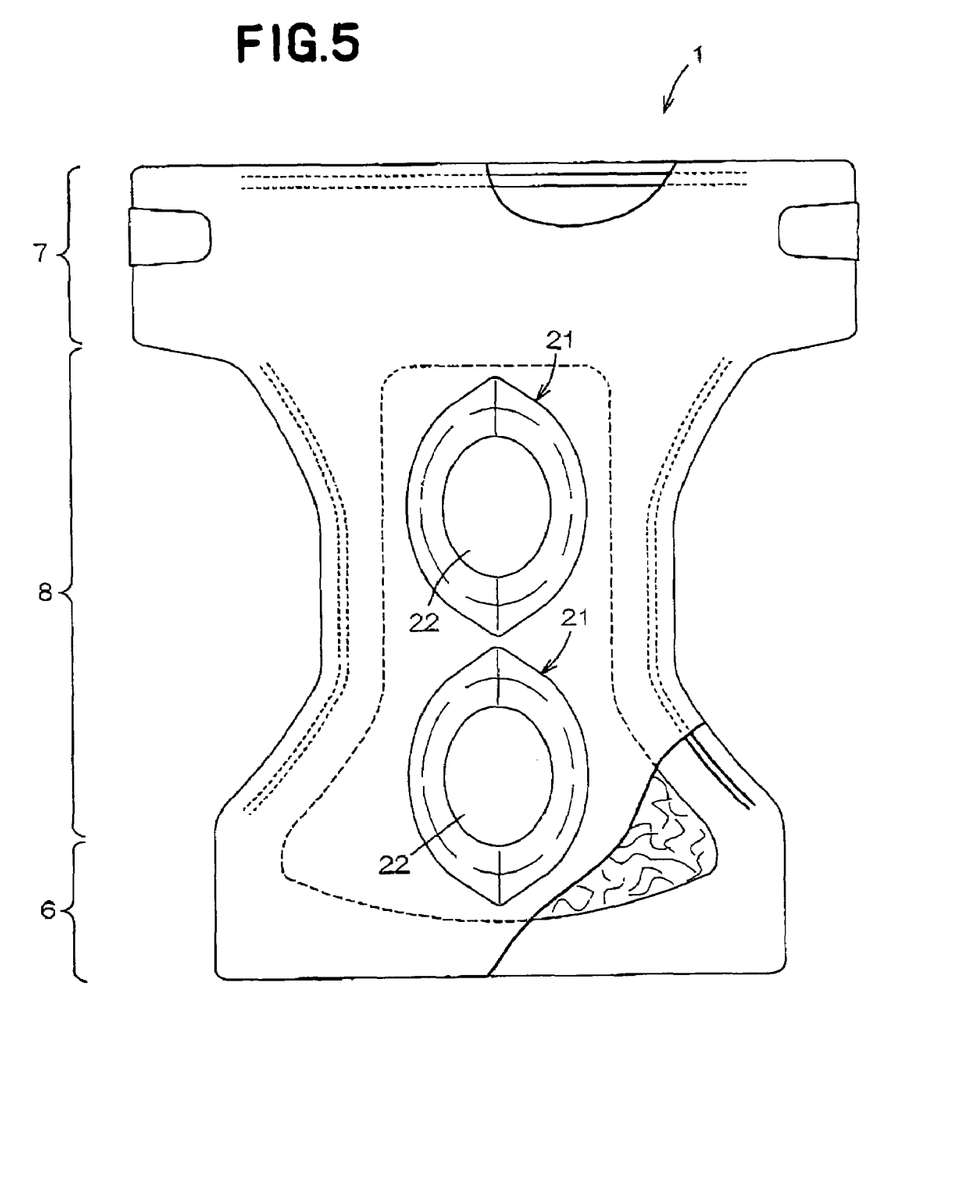
FIG. 5 is a view similar to FIG. 1 showing another embodiment of the invention.

FIG. 5 is a view similar to FIG. 1 showing another embodiment of the invention. In the diaper 1 according to this embodiment, a pair of the annular protrusions 21 are formed in the crotch region 8 at a location put aside toward the front waist region 6 and at a location put aside toward the rear waist region 7, respectively, so that these two protrusions 21 are aligned in a longitudinal direction of the diaper 1. A space 22 surrounded by the protrusion 21 located aside the front waist region 6 is adapted to receive urine.

Figure 6:
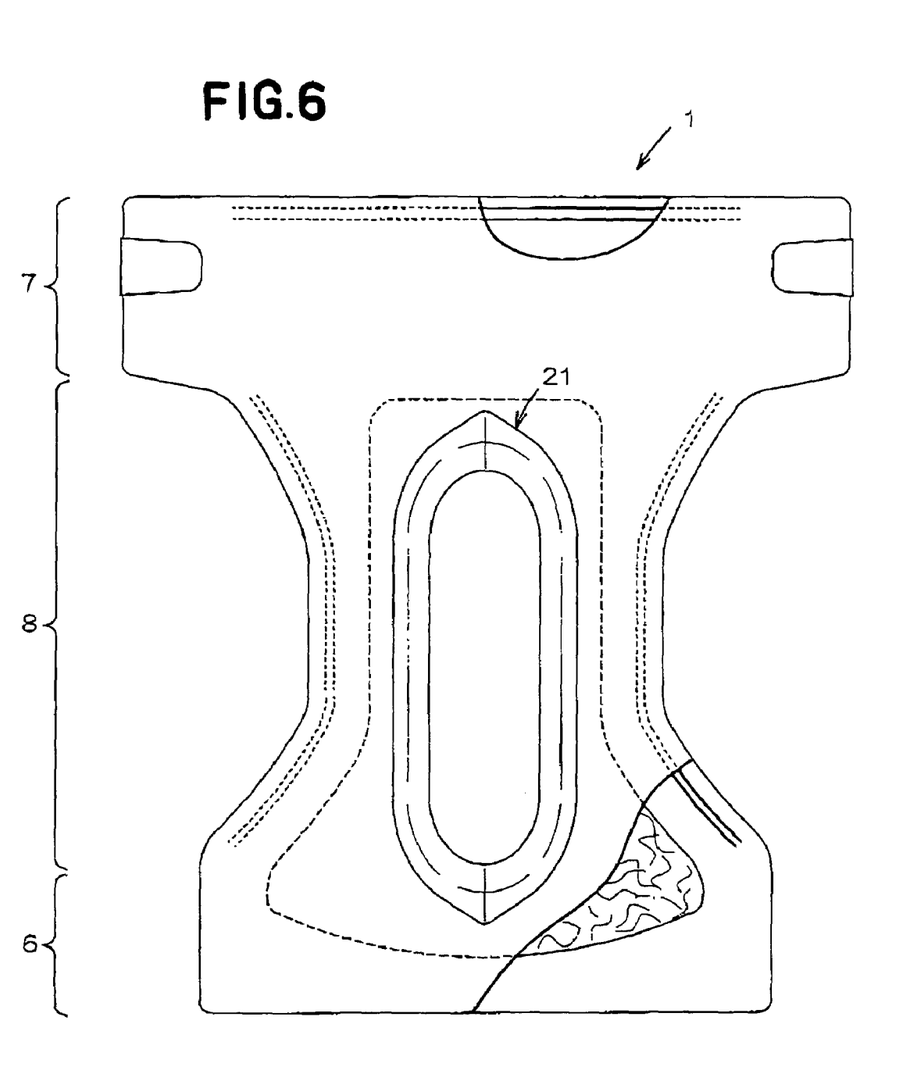
FIG. 6 is a view similar to FIG. 1 showing still another embodiment of the invention.

FIG. 6 is a view similar to FIG. 1 showing still another embodiment of the invention. In the diaper 1 according to this embodiment, the protrusion 21 has an oval planar shape fully extending over the crotch region 8 further into both the front waist region 6 and the rear waist region 7. In this diaper 1, not only feces but also urine can be received in the space defined by this single protrusion 21.

Figure 7:
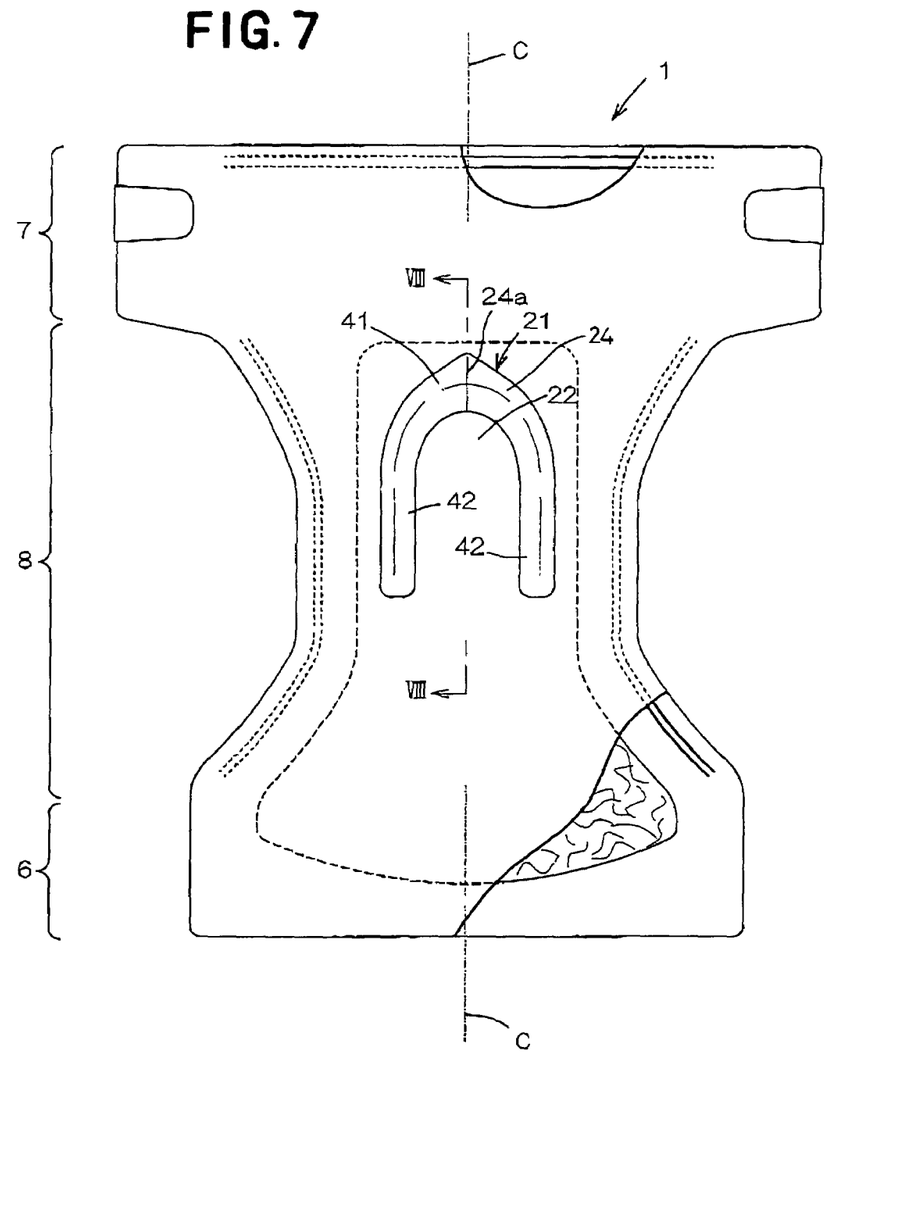
FIG. 7 is a view similar to FIG. 1 showing further another embodiment of the invention.
Figure 8:
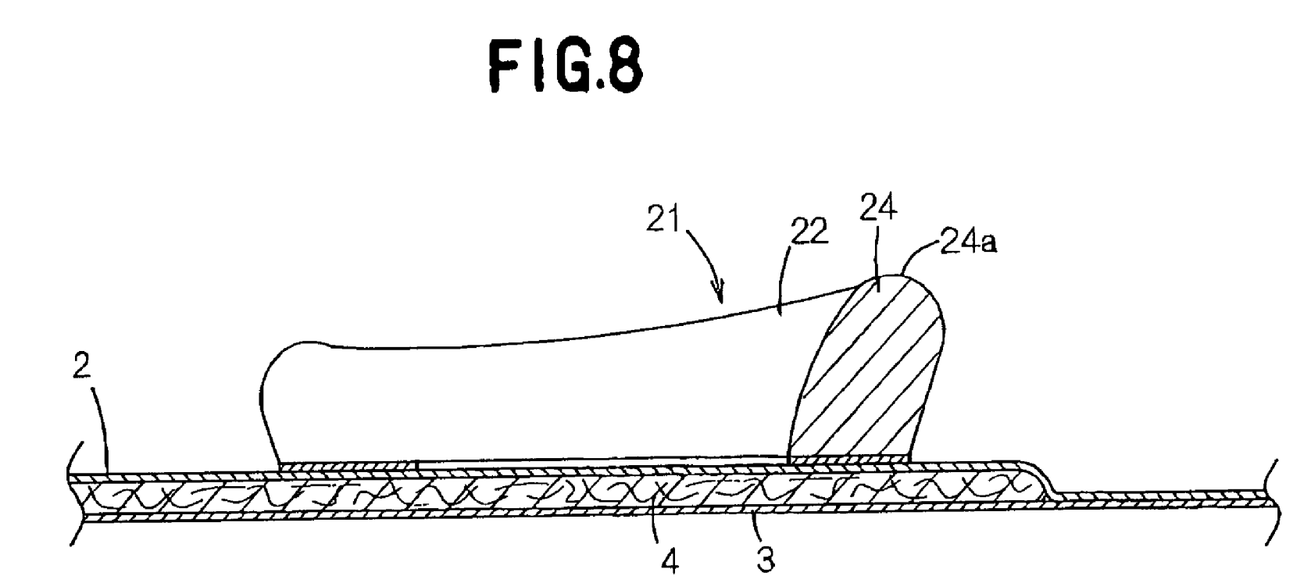
FIG. 8 is a sectional view taken along a line VIII-VIII in FIG. 7.

FIG. 7 is a view similar to FIG. 1 showing further another embodiment of the invention and FIG. 8 is a sectional view taken along a line VIII-VIII in FIG. 7. In the diaper 1 according to this embodiment, the protrusion 21 has a U-like planar shape defined by a segment 41 lying in a zone of the crotch region 8 located aside toward the rear waist region 7 transversely extending outward from the center line C-C so as to describe a curve and a segment 42 extending parallel to the center line C-C. In the protrusion 21 defined in this manner, the rear end segment 24 has its intermediate zone 24a slightly pointed. This protrusion 21 also defines the feces receiving space 22 on the inside thereof.

Figure 9:
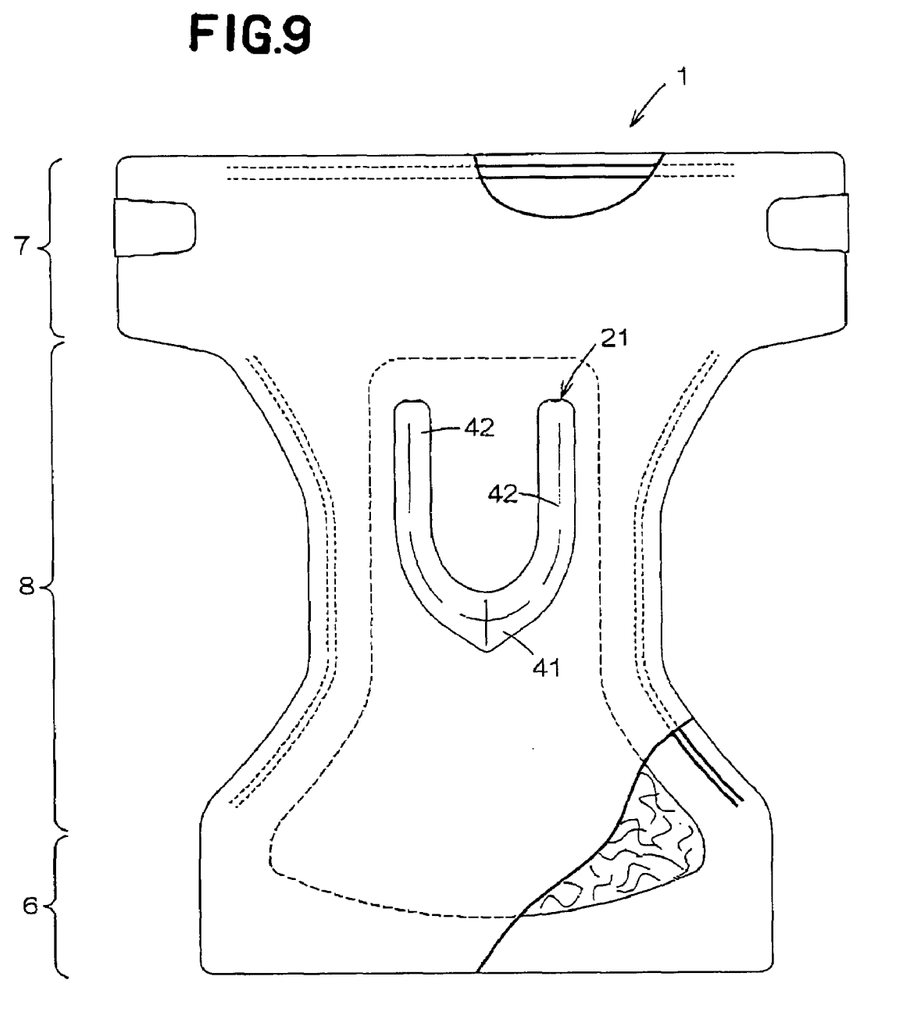
FIG. 9 is a view similar to FIG. 7 showing an alternative embodiment of the invention.

FIG. 9 is a view similar to FIG. 7 showing an alternative embodiment of the invention. The protrusion 21 of the diaper 1 according to this embodiment has a planar shape in reverse relationship with the planar shape presented by the protrusion 21 in FIG. 7. Specifically, the planar shape is defined by a segment 41 lying in a zone of the crotch region 8 located aside toward the front waist region 6 transversely extending outward from the center line C-C so as to describe a curve and segment 42 extending parallel to and connected with each other by the segment 41.

While the protrusion 21 is illustrated in each of FIGS. 1 to 9 to be the block of foamed plastic which may be directly placed against the wearer's body, it is possible to cover this block with the topsheet 2 or the other sheet and thereby to place this block indirectly against the wearer's body. In the diaper 1, a nonwoven fabric or a perforated plastic film may be used as a stock material for the topsheet 2. It is also possible to use a plastic film as a stock material for the backsheet 3 and bond a nonwoven fabric to a lower surface of this plastic film so that a touch peculiar to the plastic film may be converted to a cloth-like touch.

Figure 10:
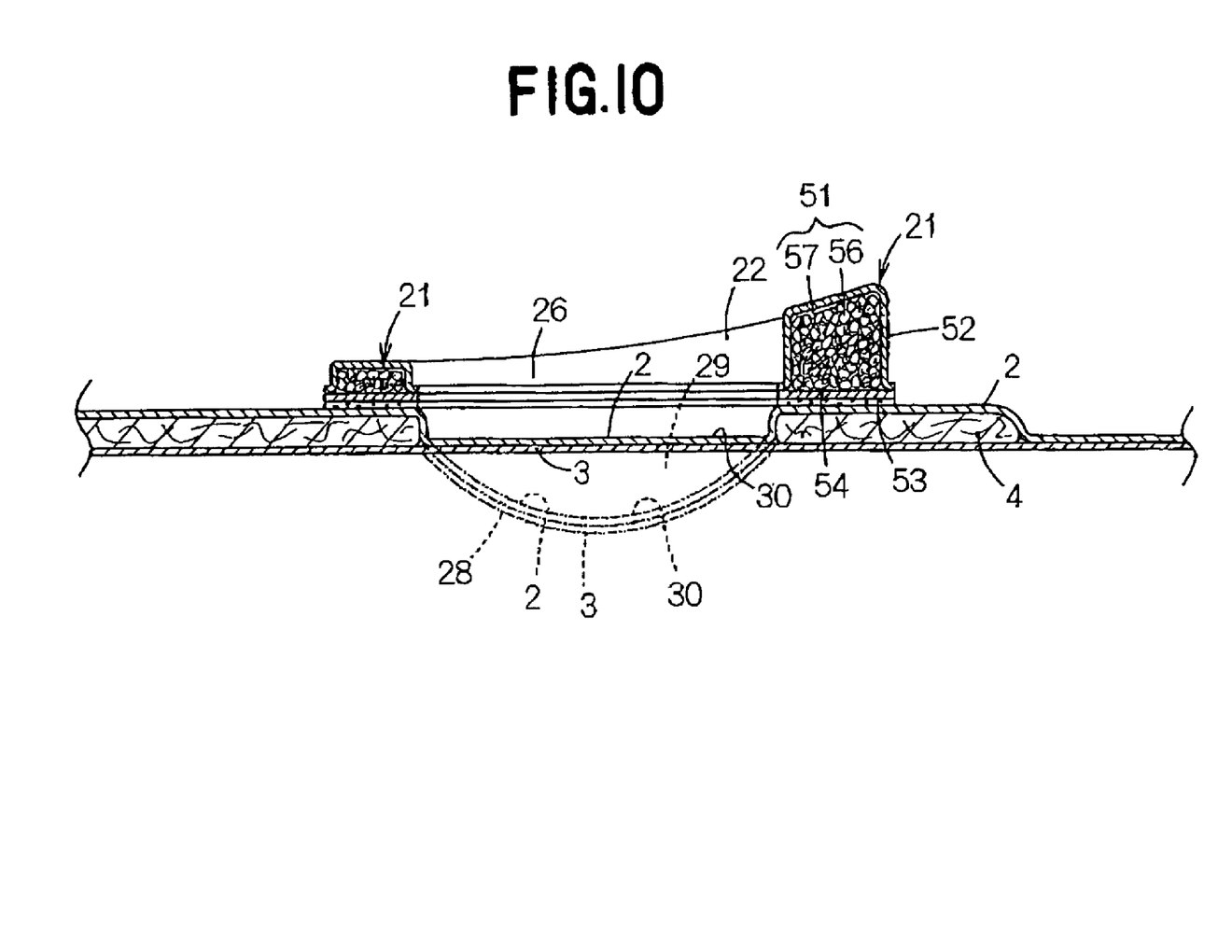
FIG. 10 is a view similar to FIG. 4 showing another alternative embodiment of the invention.

FIG. 10 is a view similar to FIG. 4 showing another alternative embodiment of the invention. In the diaper 1 according to this embodiment, the protrusion 21 comprises a cover sheet 52 defining an outer surface of the protrusion 21 and a filler 51 filling the interior of this cover sheet 52. A portion of the cover sheet 52 defining a bottom 54 of the protrusion 21 is bonded to the topsheet 2 by means of a bonding agent 53 such as an adhesive or a pressure-sensitive adhesive. The filler 51 may comprise elastic chips 56 of the same foamed plastic as the foamed plastic forming the block 50 of the protrusion 21 in the embodiment shown in FIG. 4 in a range of 60 to 100 wt % and an easily deformable thermoplastic synthetic fibrous material 57 or the like in a range of 0 to 40 wt %. Each of the chips 56 preferably has a maximum diameter in a range of 1 to 20 mm. The fibrous material 57 preferably has a fineness in a range of 0.1 to 10 dtx and a fiber length in a range of 3 to 75 mm. The fibrous material 57 may be selected from the group including nylon, polyester, conjugated fibers consisting of any one of these nylon and polyester and polyethylene, and the conjugated fibers subjected to crimping treatment. The cover sheet 52 may be formed by a preferably liquid-impervious, more preferably breathable but liquid-impervious nonwoven fabric of thermoplastic synthetic fibers or a conjugated sheet consisting of such nonwoven fabric and a plastic film laminated on an inner surface of this nonwoven fabric.

With the diaper 1 having the protrusion 21 configured in this manner, the filler 51 comprises a plurality of the elastic chips 56 each adapted to be elastically deformed and thereby to facilitate the protrusion 21 to fit the wearer's body in spite of more or less irregularities inevitably present on the body. It is possible to perform the cover sheet 52 in coincidence with the shape of the protrusion 21 and to fill the inner space defined by this protrusion-shaped cover sheet 52 with the chips 56. Compared to the case in which the protrusion 21 is provided in the form of the block of foamed plastic as in the case shown in FIG. 2, filling the inner space defined by the protrusion-shaped cover sheet 52 with the chips 56 will facilitate the protrusion 21 to be made and simultaneously reduce a cost for making the protrusion 21. The fibrous material 57 to be mixed with the chips 56 serve to adjust a degree at which the protrusion 21 is compressed and deformed under the effect of the fibrous material 57 filling gaps left among these chips 56. In other words, the fibrous material serves to adjust a compressibility of the protrusion 21. A pressure-sensitive adhesive may be used as the bonding agent to ensure that the protrusion 21 can be peeled off from the topsheet 2 as so-called nonburnables for disposal of the used diaper 1.

Figure 11:
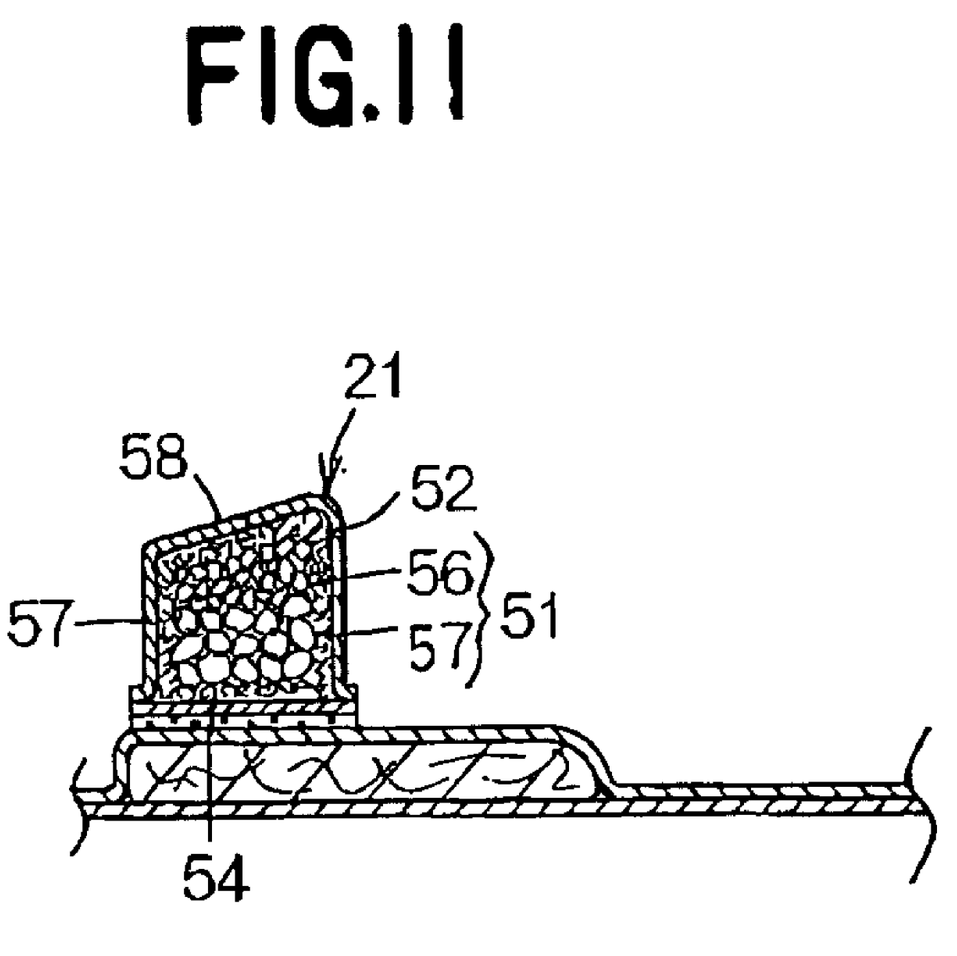
FIG. 11 is a sectional view showing important parts in still another alternative embodiment of the invention.

FIG. 11 is a sectional view showing important parts in the diaper 1 according to still another alternative embodiment of the invention and having a configuration similar to the diaper 1 of FIG. 10. Within the protrusion 21 of the diaper 1 according to this embodiment, a size of the chip 56 is uneven in such a manner that the size of the chip 56 is gradually enlarged from the top 58 toward the bottom 54 of the protrusion 21. For example, the protrusion 21 contains therein the chips 56 each having a size in order of 1 to 8 mm in a range of 30% of the full height defined aside toward the top 58, the chips 56 each having a size in order of 4 to 20 mm in a range of 40% of the full height defined aside toward the bottom 54 and the chips 56 each having a size in order of 8 to 14 mm of the full height in a range of 30% defined by the intermediate level. It is also possible to fill the space within the protrusion 21 with the chips 56 at a density gradually increasing from the top 58 toward the bottom 54. On an inner surface of the cover sheet 52, the fibrous material 57 is densely accumulated to form a layer. Such layer of the fibrous material 57 allows the protrusion 21 to offer a soft touch when it comes in contact with the wearer's body particularly around the top 58. In addition, the layer of the fibrous material 57 eliminates a feeling of irregularities of the cover sheet 52 due to the presence of the chips 56 immediately underlying the cover sheet 52 and allows the cover sheet 52 to offer a smooth touch. It should be noted here that a layer of the fibrous material 57 formed on an inner surface of the bottom 54 preferably has a flexural rigidity in a range of 0.98 to 5.0 N/25.4 mm in order that the rigidity of the bottom 54 may be sufficiently high to facilitate the bottom 54 to be easily bonded to the topsheet 2.

The disposable diaper according to the present invention is primarily characterized in that the diaper is formed on its surface facing the wearer's body with the protrusion made of flexible and elastic foamed plastic. In consequence, the protrusion tightly fits to the wearer's body and there is no apprehension that feces or urine once having been received in the space surrounded by the protrusion might leak outward beyond this protrusion and this flexible protrusion might stimulate the wearer's body. In addition, even after the protrusion has been deformed under a body weight of the wearer, the protrusion can easily restore its initial shape. Thus the desired fitness of the protrusion to the wearer's body can be ensured even when the diaper is put on the wearer's body again after the diaper has been once put off from the wearer's body and/or even when the diaper is wetted with bodily discharges.

What is claimed is:

1. A disposable wearing article, comprising:
   a front waist region, a rear waist region and a crotch region extending between said waist regions, each of said regions having an upper surface adapted to face a wearer's body and an lower surface adapted to face away from said wearer's body; and
   a tubular protrusion extending upwardly from the upper surface of said crotch region, and being sized and positioned in a transversely middle zone of said crotch region for surrounding at least one of an anus and a urethral orifice of the wearer;
   wherein
   said protrusion comprises a flexible and elastic foamed plastic material;
   said protrusion defines an opening adapted to come into contact with the wearer's body, said opening being enlarged upon compression of said protrusion in a height direction of said protrusion;
   said protrusion comprises a front end segment adjacent said front waist region, a rear end segment adjacent said rear waist region and transversely opposite lateral segments connecting and extending between said front and rear end segments; and
   a height of said protrusion gradually increases toward at least one of said front and rear end segments and is maximal at an apex on a longitudinal center line of said wearing article.

2. The wearing article according to claim 1, wherein
   a circumferential wall of said protrusion comprises a filler and a cover sheet covering the filler; and
   said filler comprises a plurality of discrete chips of said flexible and elastic foamed plastic material, said chips being arranged in multiple layers one on top another in the height direction of said protrusion.

3. The wearing article according to claim 2, wherein said chips make up 100 to 60 wt % of said filler.

4. The wearing article according to claim 3, wherein said filler further comprises thermoplastic synthetic fibers which make up at most 40 wt % of said filler.

5. The wearing article according to claim 2, wherein each of said chips has a maximum diameter in a range of 1 to 20 mm.

6. The wearing article according to claim 2, wherein a maximum diameter of the chips in each of said layers progressively increases from an upper one of said layers toward a lower one of said layers.

7. The wearing article according to claim 2, wherein a density of said chips progressively increases downwardly in the height direction of said protrusion.

8. The wearing article according to claim 2, further comprising a layer of thermoplastic synthetic fiber that underlies said chips in a vicinity of a bottom of said protrusion, wherein said layer of thermoplastic synthetic fiber has a bending stiffness in a range of 0.98 to 5.0 N/25.4 mm.

9. The wearing article according to claim 2, wherein said filler further comprises thermoplastic synthetic fibers mixed with said chips to fill gaps between adjacent said chips.

10. The wearing article according to claim 2, wherein said chips have different sizes and irregular shapes.

11. The wearing article according to claim 1, wherein said foamed plastic material is polyurethane foam having a cell population in a range of 30 to 150/25 mm, a density in a range of 20 to 120 kg/m$^3$ and an impact resilience in a range of 5 to 30%.

12. A disposable wearing article, comprising:
    a front waist region, a rear waist region and a crotch region extending between said waist regions, each of said regions having an upper surface adapted to face a wearer's body and an lower surface adapted to face away from said wearer's body; and
    a tubular protrusion extending upwardly from the upper surface of said crotch region, and being sized and positioned in a transversely middle zone of said crotch region for surrounding at least one of an anus and a urethral orifice of the wearer;
    wherein
    said protrusion comprises a flexible and elastic foamed plastic material; and
    said protrusion defines an opening adapted to come into contact with the wearer's body, said opening being enlarged upon compression of said protrusion in a height direction of said protrusion;
    said wearing article further comprising an absorbent body and a liquid-impervious backsheet underlying said absorbent body;
    said tubular protrusion being bonded to an upper surface of said absorbent body;
    said absorbent body comprising therein a through hole which is aligned with the tubular protrusion and defines together with the tubular protrusion a pocket; and
    a portion of said backsheet being exposed, at a bottom of said pocket, through said opening and said tubular protrusion.

13. A disposable wearing article, comprising:
    a front waist region, a rear waist region and a crotch region extending between said waist regions, each of said regions having an upper surface adapted to face a wearer's body and an lower surface adapted to face away from said wearer's body; and
    a tubular protrusion extending upwardly from the upper surface of said crotch region, and being sized and positioned in a transversely middle zone of said crotch region for surrounding at least one of an anus and a urethral orifice of the wearer;
    wherein
    said protrusion comprises a flexible and elastic foamed plastic material;
    said protrusion defines an opening adapted to come into contact with the wearer's body, said opening being enlarged upon compression of said protrusion in a height direction of said protrusion; and the circumferential wall of said protrusion comprises inner and outer surfaces; and a top surface connecting said inner and outer surfaces, said top surface being convex upward as viewed in a cross-section of said protrusion.

14. A disposable wearing article, comprising:

a front waist region, a rear waist region and a crotch region extending between said waist regions, each of said regions having an upper surface adapted to face a wearer's body and a lower surface adapted to face away from said wearer's body;

an absorbent body, a liquid-impervious backsheet underlying said absorbent body, and a liquid-pervious topsheet overlying said absorbent body;

a protrusion extending upwardly from an upper surface of the topsheet in said crotch region, and being sized and positioned for at least partially surrounding at least one of an anus and a urethral orifice of the wearer;

wherein said protrusion comprises a flexible and elastic foamed plastic material; and said absorbent body comprises therein a through hole which is aligned with the protrusion and defines together with the protrusion a pocket; and a portion of said backsheet is exposed, at a bottom of said pocket, through said opening and said protrusion.

* * * * *